(12) United States Patent
Atkinson et al.

(10) Patent No.: US 6,664,050 B1
(45) Date of Patent: Dec. 16, 2003

(54) VIRAL OBESITY METHODS AND COMPOSITIONS

(75) Inventors: Richard L. Atkinson, Fitchburg, WI (US); Nikhil V. Dhurandhar, Madison, WI (US)

(73) Assignee: Obetech, LLC, Fitchburg, WI (US)

( * ) Notice: Subject to any disclaimer, the term of this patent is extended or adjusted under 35 U.S.C. 154(b) by 0 days.

(21) Appl. No.: 09/619,117

(22) Filed: Jul. 19, 2000

Related U.S. Application Data

(63) Continuation of application No. 09/056,153, filed on Apr. 6, 1998, now Pat. No. 6,127,113.
(60) Provisional application No. 60/042,942, filed on Apr. 4, 1997.

(51) Int. Cl.⁷ ............................ C12Q 1/68; G01N 33/53
(52) U.S. Cl. ............................ 435/6; 435/7.1; 435/345
(58) Field of Search .................... 435/5, 7.1, 235.1, 435/6, 345; 424/233.1, 204.1; 536/23.72; 530/328, 324

(56) References Cited

PUBLICATIONS

Wigand et al. 1980, Archives of Virology, vol. 64 (3), pp. 225–233 (abstract only).*
Dhurandhar et al. Apr. 1, 1997, FASEB, vol. 11, No. 3, pp. A230.*

* cited by examiner

*Primary Examiner*—Ali R. Salimi
(74) *Attorney, Agent, or Firm*—Quarles & Brady LLP

(57) ABSTRACT source of viral induced obesity has been discovered. A virus known as AD-36P has been found to be associated with obesity in both animals and humans. Diagnostic DNA sequences are presented so that DNA based tests for the presence of the obesity associated virus can be conducted.

3 Claims, No Drawings

VIRAL OBESITY METHODS AND COMPOSITIONS

RELATED APPLICATION

This application is a continuation of patent application Ser. No. 09/056,153 filed Apr. 6, 1998, now U.S. Pat. No. 6,127,113, which claims the benefit of the provisional U.S. application Ser. No. 60/042,942 filed Apr. 4, 1997.

TECHNICAL FIELD

This invention concerns obesity in humans caused by viruses and methods and compositions for diagnosing, treating and preventing this disease.

The invention also concerns methods and compositions for reducing levels of triglycerides and cholesterol in humans.

More particularly, the invention concerns methods and compositions for diagnosing whether obesity in a human is caused by a virus or whether a person is susceptible to becoming obese because of having been infected with and obesity-causing virus, methods for testing or screening body fluids (e.g., donated human blood) for the presence of obesity-causing viruses, methods for treating and preventing viral obesity in humans, methods for preparing vaccine compositions for treating and preventing viral obesity in humans, such vaccine compositions themselves, and viruses which cause viral obesity in humans.

Further, the invention concerns methods for reducing serum levels of triglycerides and cholesterol, including low-density-lipoprotein-associated cholesterol, in humans by administration thereto of a virus which causes viral obesity in humans.

BACKGROUND OF THE INVENTION

Obesity is a serious disease of humans. A person is clinically obese if he or she has excess adipose tissue. More particularly, for purposes of this application, a person is obese if the person's body mass index equals or exceeds 27 kg/m$^2$ and the person has excess adipose tissue. In the medical arts, the quantity of adipose tissue that is "excessive" is not well defined; but certainly greater than 25% of body weight as fat in a male and greater than 30% of body weight as fat in a female would be excessive.

Obesity has a number of known and suspected etiologies. See A. Sclafani, "Animal Models of Obesity: Classification and Characterization," *Int. J. Obesity* 8, 491–508 (1984); G. A. Bray, "Classification and Evaluation of the Obesities," *Med. Clin. N. Am.* 73, 161–184 (1989).

There is a strong positive correlation of increased body weight with elevated serum levels of triglycerides (TG) and cholesterol (CHOL), including low-density-lipoprotein-associated cholesterol (LDL-CHOL). Thus, obesity, in its known forms, is often associated with elevated serum levels of these substances.

The prevalence of obesity is increasing worldwide. The prevalence in the US population remained essentially constant, at about 25%, from 1960 to 1980. The prevalence in the US population increased between 1980 and 1990 to more than 33% and continues to increase. About 90 million people in the US are obese today. Similar statistics prevail in the rest of the world.

Obesity, in people who have the disease, is associated with physical, psychological, and social problems. Complications of obesity include, among others, diabetes mellitus, hypertension, hyperlipoproteinemia, cardiac diseases (atherosclerotic disease, congestive heart failure), pulmonary diseases (sleep apnea, restrictive lung disease), cerebrovascular accidents, cancers (breast, uterus, colon, prostate), gall bladder disease (stones, infection), toxemia during pregnancy, risks during surgery (pneumonia, wound infection, thrombo-phlebitis), gout, decreased fertility, degenerative arthritis, and early mortality.

Psychological complications of obesity include poor self-image and poor body-image. These complications are due in part to the fact that obesity is socially disfavored.

The fact that obesity is socially disfavored also presents social problems for obese people. Among these is discrimination in jobs, education and marriage.

Clearly, there is a need for methods to treat or prevent obesity. Effective treatment or preventative methods likely vary among the obese depending on the etiology of the obesity which an individual has.

Thus, there is a need to understand further the various etiologies of obesity. Such understanding will lead to methods and compositions to effectively treat or prevent the disease.

Further understanding of the etiologies of obesity also will lead to reduction in the prevalence of the social stigma associated with the disease, as it will allow the public at large to understand better that obesity is a disease which might afflict anyone and from which people do not choose to suffer. Such understanding also will allow obese persons to be convinced that they are unwilling victims of a disease, to understand through various diagnostic tests based on understanding of etiologies of the disease what the underlying cause of their obesity is, and in some cases to learn how to effectively treat the disease. Reduction in the prevalence of the social stigma associated with obesity and increased understanding among the obese concerning the disease will diminish the psychological complications and social problems which affect obese persons because of the disease.

Still further, understanding of the etiologies underlying obesity and the corresponding recognition that obesity is a disease eventually will lead medical insurance companies, which now at least in the United States typically do not recognize the condition as a disease, to recognize it as such and reimburse persons for diagnosis and treatment of it in the same way that the companies now do so for conditions that have long been recognized as diseases.

There has been speculation that one etiology of obesity in humans might be viral. A. Sclafani, supra. However, there has been no convincing evidence to support this speculation. Heretofore no virus has been identified as a cause of the disease in humans.

SUMMARY OF THE INVENTION

We have discovered that some obesity in humans is caused by viruses.

We have identified a human virus which infects or has infected about 15–20% of obese persons in the general population.

Further we have discovered that humans who suffer from viral obesity (i.e., obesity caused by a virus) have, on the average, significantly lower TG, CHOL and LDL-CHOL levels than persons who suffer from obesity that is not viral. In fact, the average TG, CHOL and LDL-CHOL levels of persons with viral obesity are within the normal ranges for persons who are not obese.

Our discoveries are bases for the various methods and compositions of the invention as described below in detail.

DETAILED DESCRIPTION OF THE INVENTION

We have found that certain adenoviruses, but not all adenovitruses, that infect humans cause obesity in humans that are infected therewith and, at the same time, lower the average TG, CHOL and LDL-CHOL levels in those who are infected.

Screening of human adenoviruses for those that cause obesity and "reduced cholesterol levels" (by which is meant herein TG, CHOL and LDL-CHOL levels that in an infected population are reduced on the average compared to a control population of obese individuals who are not infected with a virus of interest) in humans is done by methods known in the art. Namely, in a preferred method, first by antibody-screening a group of persons (e.g., more than about 10, preferably more than about 50, and more preferably more than about 100) is identified who have been infected by a particular strain of adenovirus and who are both obese and have, as a group, a mean cholesterol level that is reduced, as decribed above in this paragraph. Such an adenovirus strain is a "candidate virus." Then, to determine whether a candidate virus is one that causes obesity and reduces cholesterol levels, the virus is tested by methods recognized in the art, by infecting a group of animals such as chickens, mice, rats or monkeys, with the virus in order to test the virus for the ability to cause obesity and reduce cholesterol levels on the average in the group of infected animals. A candidate virus, which on testing in a group of animals does cause obesity and reduce the average cholesterol level in the group, is one which causes obesity and reduces cholesterol levels in humans and provides a basis for developing methods and compositions for diagnosing and treating obesity, screening for obesity-causing virus, and reducing cholesterol levels, in humans as understood in the art and described more fully hereinafter. These methods and compositions using any obesity-causing, cholesterol reducing adenovirus that infects humans are encompassed by the present invention.

By applying the foregoing methods, we have found that human adenoviruses Ad-2 and Ad-31, which are available from the American Type Culture Collection ("ATCC"), do not cause obesity or reduce cholesterol levels in humans but that adenovirus Ad-36, which is also available from the ATCC, and a variant thereof that we have isolated, adenovirus Ad-36p, do do so.

Thus, in one of its aspects, the invention is substantially isolated human adenovirus Ad-36P.

"Substantially isolated" is defined herein with reference to a sample of viruses that is in an in vitro system such as a culture, a plate on which culture is grown, a suspension in buffer or culture medium, a band on a gel, a pellet resulting from centrifugation of a suspension comprising virus, or the like and that comprises one or more variants of human adenovirus strain Ad-36 as available from the ATCC (Rockville, Md., USA) under accession no. VR-913.

We have found that strain Ad-36 as obtained from the ATCC comprises a number of variants of the virus. One of these variants is adenovirus Ad-36P. Thus, by "substantially isolated" is meant that the virus is in an in vitro system as described above and, in the system, the ratio of the number of particles of Ad-36P to the number of particles of all variants of strain Ad-36 is greater than such ratio in strain Ad-36 obtainable from the ATCC under accession no. VR-913.

Preferably, of course, a sample of Ad-36P in an in vitro system will consist essentially of virus particles of that variant alone, as might be obtained for example by standard passaging at least three times of strain Ad-36 as obtained from the ATCC.

Strain Ad-36p is readily available to the art, as it can be isolated from some humans who are obese and who have reduced cholesterol levels (as indicated above, in comparion with obese persons who are not infected with an obsesity-causing, cholesterol-level-reducing adenovirus).

Herein below we present the nucleotide sequence of cDNA that encodes the fiber protein of strain Ad-36p. This sequence further serves to identify the strain.

We have discovered adenovirus Ad-36P to be surprisingly sensitive, and specifically more sensitive than Ad-36 as obtained from culture obtained from the ATCC, in detecting serum antibody that reacts with Ad-36.

Adenovirus Ad-36P, like Ad-36, when it infects a person, causes the person to become obese with an obesity characterized by TG, CHOL and LDL-CHOL levels that, on the average in the infected population, are reduced compared to obese persons who are not infected with obesity-causing virus and in fact, in some obese and infected individuals (typically ones who are not severely obese) are not elevated above the normal levels in persons who are not obese.

In another of its aspects, the invention is an anti-obesity vaccine which comprises as the active ingredient a composition selected from the group consisting of: (i) killed virus and inactivated live virus, wherein the corresponding live (non-inactivated) virus infects humans, and causes obesity and reduced cholesterol levels in individuals infected with the virus; (ii) a coat protein of the coat of such a virus; (iii) an immunogenic peptide with from about 6 to about 30 amino acids in a sequence which comprises the sequence of an epitope of such a coat protein; (iv) nucleic acid (DNA or RNA) with a sequence which encodes such a coat protein or such an immunogenic peptide; and (v) a non-pathogenic virus, such as a vaccinia virus or fowl-pox virus, which is genetically modified to have a modified coat protein which comprises in immunogenic position and orientation a segment with the sequence of a coat protein of a virus which infects humans and causes obesity and reduced cholesterol in infected individuals or a sequence of a peptide of from about 6 to about 30 amino acids in a sequence which comprises the sequence of an epitope of a virus which infects humans and causes obesity and reduced cholesterol in infected individuals.

The various active ingredients in the vaccines of the invention are either immunogenic per se or provide in vivo in a vaccinated person protein or peptide which is immunogenic. Peptides of 6–30 amino acids, to be rendered acceptably immunogenic, might require modification by any of various techniques known in the art (e.g., conjugation with a large protein).

The various vaccines in accordance with the invention are all prepared by methods known in the art.

From the adenoviruses which can be the bases for an anti-obesity vaccine according to the invention, because they infect humans and cause obesity and reduced cholesterol levels on the average in infected individuals (among these Ad-36p being the most preferred), hexon or fiber proteins, preferably the fiber protein, or segments of the fiber protein, as indicated above, can be used as the immunogen.

By the term "immunogenic," with reference to an anti-obesity vaccine of the invention, is intended capability to provoke in a person to whom the vaccine is administered an immune response that yields neutralizing antibodies against an obesity-causing, live virus that might infect the person after administration of the vaccine.

The anti-obesity vaccines of the invention, wherein the immunogenic component is live, inactivated virus, killed virus, coat protein per se, epitope-comprising coat protein segment, or coat protein (or epitope-comprising segment thereof) provided with use of a non-pathogenic, genetically modified carrier virus such as a vaccinia virus or a fowl pox virus, are prepared using methods well known in the art. Thus, the vaccines will include carriers, excipients, adjuvants, antimicrobials, preservatives and the like as well understood in the art. Thus, in addition to the active ingredient, the vaccines will have suitable compositions, usually aqueous buffers, such as phosphate-buffered saline or the like, in which the active ingredient will be suspended along with, optionally, any of various immune-system stimulating adjuvants used in human vaccine preparations, antimicrobial compositions, and other compositions to stabilize the preparations. All compositions included with the vaccine preparation will be suitable for administration to humans. The vaccine preparation may be stored in lyophilized form and then combined with solution soon before administration. For oral administration, the vaccine preparation may be in solution, tablet or pill form optionally with an enteric coating as understood in the art. The concentration of active (immunogenic or immunogen-providing) component in solution with which it is administered typically will be between about 1 ng and about 1 mg/ml.

The anti-obesity vaccines of the invention will be administered intranasally, orally, or by injection intravenously, intramuscularly, subcutaneously or peritoneally.

Administration of the vaccines of the invention is to be under the guidance of a physician.

Appropriate dosing of the anti-obesity vaccine is well within the skill of medical practitioners and will depend on a number of factors including the age of the person being treated, the urgency of the person's developing protective immunity, the status of the person's immune system, and other factors known to the skilled. The vaccine typically will be administered in several steps in order to cause and maintain protective immunity against obesity-causing virus in the person being vaccinated. Thus, after the primary vaccination, there typically will be between one and about ten booster vaccinations separated by periods between about 1 week and 10 years.

A single dose of an anti-obesity vaccine of the invention (in solution form) will have a volume of between about 0.1 ml and 10 ml and, in any form, will have between about 1 ng and 10 mg of killed or inactivated obesity-causing virus, between about 1 ng and 10 mg of genetically modified, non-pathogenic virus, or between about 1 ng and 10 mg of coat protein (e.g., fiber protein) or 6–30 amino acid peptide (in its form as modified to be immunogenic).

An anti-obesity vaccine of the invention, wherein the active ingredient is nucleic acid, will also be a standard preparation for vaccines of that type. With vaccines of this type, the nucleic acid is not the immunogen but is expressed in vivo after administration of the vaccine as a peptide or protein which in turn is immunogenic. Vaccines of this type will be administered by techniques known in the art for such vaccines (e.g., intramuscular injection). Dosing will also be according to procedures known in the art to cause and maintain protective immunity against viral obesity in the vaccinated individual.

Note that an anti-obesity vaccine according to the invention may include active ingredients based on more than one obesity-causing virus (or the coat protein (e.g. fiber protein) or epitopic segments of the coat protein thereof).

In yet another aspect, the invention is a method of preventing obesity caused by a virus in a human susceptible thereto which comprises administering to the human an amount of an anti-obesity vaccine of the invention that is effective to raise and maintain a protective immune response against an obesity-causing adenovirus.

In still another aspect, the invention entails a method of reducing the serum levels of triglyceride, (total) cholesterol and low-density-lipoprotein-associated cholesterol in a person with above normal serum levels thereof which comprises administering to the person an amount effective for such purpose of a live virus which infects humans and causes obesity in infected individuals.

"Normal" serum levels are as follows: triglycerides (TG): less than 150 mg/dL; (total) cholesterol (CHOL): less than 200 mg/dL; low-density-lipoprotein-associated cholesterol (LDL-CHOL): less than 130 mg/dL.

In a preferred application of this method of the invention, the TG, CHOL and LDL-CHOL levels would all be reduced to normal levels.

This method of the invention could especially advantageously be applied to persons who are at very high risk of complications or death from atherosclerotic disease or congestive heart failure because of high serum levels of triglyceride (hypertriglyceridemia) or cholesterol (hypercholesterolemia).

The method is carried out by administering the live virus, or a more preferably a fragment of the virus such as the E 1A fragment which is a well known fragment of adenoviruses, in a conventional medium that is acceptable for administration to humans, to the person being treated in one or more doses sufficient to infect the person with the virus. The administration can be intranasal, oral, or by injection intravenously, subcutaneously, intramuscularly, or peritoneally.

Among the live viruses that can be employed in this method of the invention are obesity-causing, cholesterol-level-reducing, human adenoviruses, such as Ad-36 and Ad-36P, and the E1A fragments thereof. E1A fragments may be delivered intracellularly in a person being treated by methods known in the art using innocuous viruses, such as vaccinia viruses or retroviruses (modified so as to be non-infectious). The innocuous viruses used in accordance with the invention will have genomes that are modified to include DNA that encodes the E1A fragment in a position where the fragment will be expressed in cells of the individual that have been infected with the innocuous virus. The innocuous virus, so modified, will be administered to an individual being treated so as to infect the individual (and cells of the individual) with the virus. As described hereinabove, as known in the art, DNA itself(in an appropriate solution) which comprises a segment that encodes the EIA fragment may be injected directly into an individual being treated to provide E1A intracellularly in the individual.

In still another aspect, the invention entails methods for diagnosing whether a non-obese person is at risk of acquiring viral obesity, a method for diagnosing whether an obese person suffers from viral obesity, and a method of screening body fluids or organs and tissues (especially donated blood or donated organs or tissues) for the presence of obesity-causing adenoviruses. These methods of the invention comprise analyzing, by any conventional immunoanalytical or nucleic-acid probe hybridization based procedure, a sample of blood, other body fluid, feces, tissue or organ for the presence of antibody reflecting infection with the virus, the presence of a protein (e.g., a fiber protein) characteristic of the presence of the virus, or the presence of a nucleic acid fragment characteristic of the presence of the virus.

As understood in the art, a person whose blood, other body fluids, feces, or tissues or organs has been or is infected with the virus but who is not obese will be at greater risk than a person who has not been or is not so infected of becoming obese on account of infection by the obesity-causing virus and might be treated early to slow or prevent the onset of the disease. Similarly, an obese person whose blood, other body fluids, feces, or tissues or organs has been or is infected with the virus can ascribe his or her obesity at least in part to infection with the obesity-causing virus and, for example, might suffer less severe psychological or social trauma by understanding that he or she is suffering from an obesity that is a conventional disease or may demand reimbursement from his or her insurance company for having a type of obesity that is a conventional disease, caused by infection with a disease-causing virus. Also, the risk of spreading viral obesity to persons who are not infected with obesity-causing virus would be drastically reduced by screening of blood by blood banks, of blood that is donated for use by others than the donees, or screening of tissues or organs by tissue and organ banks or collecting agencies, of tissues or organs donated for transplantation, for the presence, past or present, of obesity-causing virus so that such blood, tissues or organs will not be used after having been donated.

The immunoanalytical techniques that might be used in these methods are standard virus neutralization assay techniques or enzyme immunoassay techniques made possible by the availability of obesity-causing viruses identified and made available by the present invention. Antibodies against these viruses or fragments thereof (e.g., fiber protein or fragments thereof), or proteins (or fragments thereof) from these viruses for use in these immunoassay techniques can be prepared by conventional techniques well known in the art.

Similarly, the nucleic acid probe hybridization assay techniques used in these methods of the invention will be standard techniques (optionally after amplification of DNA or RNA extracted from a sample of blood, other body fluid, feces, tissue or organ) using nucleic acid probes (and primers if amplification is employed) made available by the obesity-causing viruses identified and made available by the present invention. The sequences of nucleic acids characteristic of these viruses can be determined by standard techniques once the viruses are conventionally isolated, and probes and primers that are specific for the viruses and that provide the basis for nucleic acid probes and primers that can be used in nucleic acid based assays for the viruses are prepared using conventional techniques on the basis of the sequences.

As the skilled will understand, more than one strain of obesity-causing virus may be tested for simultaneously in an immunological or nucleic acid-based assay method for testing for virus in accordance with the invention and kits may be assembled to facilitate carrying out the methods for a particular virus or a plurality of them.

Further details on carrying out the inventor are now provided in the following examples, which are illustrative and should not be construed to limit the scope of the invention.

EXAMPLE 1

Serum cholesterol (total)(TG) is determined using fasting serum, 10 microliter samples, in a cholesterol-oxidase-peroxidase method employing a kit from Sigma Chemical Co., St. Louis, Mo., USA (Cat No. 352-SOOP).

Serum triglyceride (TG) is determined using fasting serum, 10 microliter samples, in a glycerol-3-phosphate peroxidase method employing a kit from Sigma Chemical Co. (Cat. No. 339–50).

Serum high-density-lipoprotein-associated cholesterol (HDL-CHOL) is determined using fasting serum with a kit from Sigma Chemical Co.

Low-density-lipoprotein-associated cholesterol (LDL-CHOL) is determined using the equation

LDL-CHOL=(CHOL)−(HDL-CHOL)−(TG/5).

EXAMPLE 2

Ad-36 virus was obtained from the ATCC (American Type Culture Collection), Accession No. VR-913. The virus was grown in A549 bronchial human carcinoma cells (Wisconsin State Laboratory of Hygiene, University of Wisconsin, Madison, Wis., USA). Plaques were grown, and a single plaque was removed and used to reinfect a fresh batch of A549 cells. Plaques of this second passage were grown and again a single plaque was picked and used to reinfect another fresh batch of A549 cells. The resulting virus is Ad-36P.

In virus neutralization assays of 5 human sera known to have antibodies to Ad-36 (ATCC VR-913), Ad-36p showed a 2-to 4-fold greater titer for neutralizing antibodies than did Ad-36. This demonstrates the greater sensitivity of Ad-36p, as compared to Ad-36, in assaying serum for antibody against obesity-causing adenoviruses.

EXAMPLE 3

Minimum Essential Media Eagle (MEM)(Sigma Chemical Co. Cat. No. M-0643) with non-essential amino acids, Earle's salts, 1-glutamine, 10% fetal bovine serum and 2.9% sodium bicarbonate (v/v), pH 7.4, is used for growing A549 cells. 5 to 10 microliters of virus stock solution is mixed with 8 ml of the medium and the mixture is pipetted into flasks with growing cells. The flasks are incubated for 1 h at 37 deg. C. while shaking gently every 15 min. After 1 h, the medium is removed and replaced with fresh medium, The flasks are then incubated at 37 deg. C. The cells are grown over 7 to 8 days, until 90% of the cells show CPE. The cell material and medium are then centrifuged at 1000 rpm for 15 min to eliminate cell debris. The supernatant with virus (e.g., Ad-36 or Ad-36P), is again centrifuged at 1000 rpm for 10 min and then aliquoted into 2 ml cryovials for storage at −70 deg. C. until use.

EXAMPLE 4

Fiber protein is isolated from virus in a two step procedure. First, virus is purified from supernatant (see Example 3) using CsCl gradient centrifugation, following the procedure described by Graham and Ludvik in Chapter 11 of *Methods in Molecular Biology*, Vol. 7: *Gene transfer and Expression Protocols*, E. J. Murray, ed., The Humana Press, Inc., Clifton, N.J. (1991). Then the fiber protein is isolated from the virus electrophoretically following Oostrum and Burnett, *J. Virology*, 56,439448 (1985) and Maizel et aL, *Virology*, 36, 115–125 (1968).

The electrophoretic band of fiber protein (approx. mol. wt. 60,000 daltons) is cut from the gel and the fiber protein can be isolated from the band by standard techniques.

EXAMPLE 5

A virus neutralization assay (serum neutralization assay) is used to assay serum for antibody reactive with adenovirus in serum of test subjects.

Serum is thawed and heat-inactivated for 30 min. at 56 deg. C.

The assay is carried out in standard 96-well microtiter plates. Serial two fold dilutions (1:2 to 1:1024) are made with the medium that is the A549 growth medium described in Example 3 but lacks the fetal calf serum and sodium bicarbonate. 50 microliters of each dilution is added in duplicate to the wells of the plate. 50 microliters of virus suspension (100 TCID$_{50}$)is then added to each well. (TCID$_{50}$ is calculated by serially diluting viral stock solution and inoculating A549 cells with the dilutions to determine the reciprocal of the highest dilution of virus which causes CPE in 50% of the material inoculated.) The plates are then incubated at 37 deg. C. for 1 hr. Then 100 microliters of A549 cell suspension, containing approximately 20,000 cells, is added to each well and the plate is further incubated at 37 deg. C. for 12 days. Crystal violet-ethanol is then added to each of the wells to fix and stain the cells and the plates are examined macroscopically for CPE;. The highest serum dilution with no CPE is the titer. Controls used in the procedure are wells with no virus and wells with virus but no serum. A back titration is carried out to confirm that appropriate virus dilutions were used. Positive control is antisera to chicken adenovirus and human adenovirus. Presence of CPE with the virus and no CPE in the presence of serum is considered an indication of effective neutralization of the virus with antibody in serum, such that the serum is considered to have antibody against the virus. A titer of 1:8 or greater is considered positive.

The foregoing assay was carried out on serum samples from 155 obese patients and 45 non-obese volunteers. 15–20% of the obese patients were positive for antibody. All of these had TG, CHOL, and LDL-CHOL within the normal ranges for non-obese people. The remaining obese people (antibody-negative) had, on the average, TG, CHOL and LDL-CHOL levels above the normal ranges for non-obese people. None of the non-obese volunteers was positive for antibody. The non-obese volunteers had, on the average, TG, CHOL and LDL-CHOL levels that were in the normal ranges for non-obese people.

EXAMPLE 6

Ad-36P virus is killed by adding 42 microliters of 37% formalin to 150 microliters of virus stock, then incubating the resulting composition at room temperature for 72 hours, and finally adding 15 microliters of 35% sodium bisulfite. Confirmation that the virus was killed is carried out by inoculating a culture of A549 cells with the final solution and determining that virus does not grow in the culture.

EXAMPLE 7

Nucleic acid from adenovirus Ad-36p was isolated and sequenced by a standard sequencing method.

The cDNA sequence encoding the fiber protein is as follows (SEQ ID NO:1): 5'-ATGTCAAAGAGGCTCCGGGTGGAAGATGACTT CAACCCCGTCT ACCCCTATGGCTACGCGCGGAAT- CAGAATATCCCCTTCCTCACT CCCCCCTTTGTCTC- CTCCGATGGATTCCAAAACTTCCCCCCTGG GGTC- CTGTCACTCAAACTGGCTGATCCATGTCTCACTC AAGGTG GGAGGGGGACTCACTGTAGAACAA- CAGTCTGGAAAACTGAGTG TGGATACTAAGGCAC- CCTTGCAAGTTGCAAATGACAACAAATT GGAGC- TATCTTATGATGATCCATTTAAGGTAGAGAATAA CAAA CTTGGAATTAAAGCTGGCCATGGTTTAG- CAGTTGTAACTAAAGA AAACACAAGTCTTC- CTAGTCTAGTTGGAACACTTGTAGTTTTAA CTG- GAAAAGGAATAGGTACTGGATCAAGTGCACATG GAGGAAC TATTGATGTAAGACTTGGTGAAGGAG- GTGGGTATCATTTGATG AAAAAGGAGACTTAG- TAGCTTGGGACAAAAAAAATGATACACG CAC- CCTTTGGACAACACCTGATCCTTCTCCAAATTGC AAGTTG AAACAGCAAGAGACTCAAAGCTAACCT- TAGCACTTACAAAATG TGGTAGTCAAATTTTGGC- CACTGTATCTTTACTTGTTGTTACGGG CAAATATGC- TATTATAAGTGACACAGTCAACCCAAAGCAGTTCT CTATTAAGTTACTGTTTAATGA- CAAGGGTGTTTTGTTAAGTGAC TCAAATCT- TGATGGGACATATTGGAACTATAGAAGCAACAATA ACAACATAGGCACTCCTTATAAAGAG- GCTGTTGGTTTTATGCCA AGCACAACAGCTTATC- CTAAGCCAACCAACAACACCAGCACAG ATCCG- GATAAAAAAGTGAGTCAAGGTAAAAATAAAAT TGTAAG CAATATATCTTGGAGGAGAGGTATAT- CAACCAGGATTTATTG TTGTTAAATTTAATCAG- GAAACTGATGCCAATTGTGCATACTCT ATTA- CATTTGATTTGGATGGGGTAAGGTGTATAAGGA TCCTAT ACCATATGATACCTCTTCTACTTTCT- CATATATCGCTCAAGA ATGA

EXAMPLE 8

The cDNA sequence of the Ad-36p genome was screened against all known cDNA sequences and two 25-base sequences and one 28-base sequence were found, all lying in the fiber-encoding sequence provided above in Example 7, that were unique to Ad-36p. These three sequences are as follows:

SEQ ID NO:2: 5'-AGTTGAAACAGCAAGAGACTCA AAG

SEQ ID NO:3 5'-GGTACTGGATCAAGTGCACATGG AG

SEQ ID NO:4 5 '-TTGAAACAGCAAGAGACTCAAA GCTAAC

Sequence 3 above was employed a a probe for AD-36p in a conventional nuclei acid probe hybridization assay of DNA isolated from four chickens, two of which had been infected with the virus and became obese and two of which had not been infected and were not obese. DNA hybridizing to the probe was observed with only the DNA from the two infected chickens. The assay involved direct detection and was by capillary electrophoresis using laser-induced fluorescence for detection. More particularly, a replaceable polyacrylamide matrix was employed in the electrophoretic separation and detection employed a dual system with 5'-labeling of the oligo and thiazole orange intercalator in the buffer system. See Kolestar et al., J. Chromatography B, 697, 189–194 (1997).

The skilled will understand that probes, and primers when amplification is also used, of between about 15 and 30 bases in length are advantageously employed to provide suitable specificity and sensitivity.

Amplification methods using PCR and variations thereof maybe employed, as well known in the art.

What we claim is:

1. A method of determining whether an obese person is suffering from viral obesity caused by adenovirus type 36p, the method comprising the steps of isolating from the person a sample selected from the group consisting of a body fluid, feces, a sample of tissue and a sample of an organ from the person, obtaining an antibody specific to an adenovirus type 36p, and; assaying the sample using the antibody to test for the presence of the adenovirus type 36p thus testing whether the person has been or is infected with adenovirus type 36p, which causes obesity and reduces cholesterol level in humans.

2. The method according to claim 1 wherein the substance analyzed is blood.

3. A method for the detection of virally caused obesity in an obese subject comprising the steps of isolating a sample of biological tissue or fluid from the subject;

providing an antibody specific to adenovirus type 36p;

testing the sample, using the antibody diagnostic for adenovirus type 36p; and detecting the presence of adenovirus type 36p to determine if the subject has viral induced obesity.

* * * * *

SEQUENCE LISTING

<160> NUMBER OF SEQ ID NOS: 4

<210> SEQ ID NO 1
<211> LENGTH: 1096
<212> TYPE: DNA
<213> ORGANISM: Adenovirus type 36P

<400> SEQUENCE: 1

| | | | | | | |
|---|---|---|---|---|---|---|
| atgtcaaaga | ggctccgggt | ggaagatgac | ttcaaccccg | tctaccccta | tggctacgcg | 60 |
| cggaatcaga | atatcccctt | cctcactccc | ccctttgtct | cctccgatgg | attccaaaac | 120 |
| ttccccctg | gggtcctgtc | actcaaactg | gctgatccat | gtctcactca | aggtgggagg | 180 |
| gggactcact | gtagaacaac | agtctggaaa | actgagtgtg | gatactaagg | cacccttgca | 240 |
| agttgcaaat | gacaacaaat | tggagctatc | ttatgatgat | ccatttaagg | tagagaataa | 300 |
| caaacttgga | attaaagctg | gccatggttt | agcagttgta | actaaagaaa | acacaagtct | 360 |
| tcctagtcta | gttggaacac | ttgtagtttt | aactggaaaa | ggaataggta | ctggatcaag | 420 |
| tgcacatgga | ggaactattg | atgtaagact | tggtgaagga | ggtgggttat | catttgatga | 480 |
| aaaaggagac | ttagtagctt | gggacaaaaa | aaatgataca | cgcacccttt | ggacaacacc | 540 |
| tgatccttct | ccaaattgca | agttgaaac | agcaagagac | tcaaagctaa | ccttagcact | 600 |
| tacaaaatgt | ggtagtcaaa | ttttggccac | tgtatcttta | cttgttgtta | cgggcaaata | 660 |
| tgctattata | agtgacacag | tcaacccaaa | gcagttctct | attaagttac | tgtttaatga | 720 |
| caagggtgtt | ttgttaagtg | actcaaatct | tgatgggaca | tattggaact | atagaagcaa | 780 |
| caataacaac | ataggcactc | cttataaaga | ggctgttggt | tttatgccaa | gcacaacagc | 840 |
| ttatcctaag | ccaaccaaca | acaccagcac | agatccggat | aaaaagtga | gtcaaggtaa | 900 |
| aaataaaatt | gtaagcaata | tttatcttgg | aggagaggta | tatcaaccag | gatttattgt | 960 |
| tgttaaattt | aatcaggaaa | ctgatgccaa | ttgtgcatac | tctattacat | ttgatttgg | 1020 |
| atggggtaag | gtgtataagg | atcctatacc | atatgatacc | tcttctttta | ctttctcata | 1080 |
| tatcgctcaa | gaatga | | | | | 1096 |

<210> SEQ ID NO 2
<211> LENGTH: 25
<212> TYPE: DNA
<213> ORGANISM: Adenovirus type 36P

<400> SEQUENCE: 2
agttgaaaca gcaagagact caaag                                              25

<210> SEQ ID NO 3
<211> LENGTH: 25
<212> TYPE: DNA
<213> ORGANISM: Adenovirus type 36P

<400> SEQUENCE: 3
ggtactggat caagtgcaca tggag                                              25

<210> SEQ ID NO 4
<211> LENGTH: 28
<212> TYPE: DNA
<213> ORGANISM: Adenovirus type 36P

```
-continued

<400> SEQUENCE: 4
ttgaaacagc aagagactca aagctaac                                            28
```